United States Patent
Kodama

(10) Patent No.: US 10,603,476 B2
(45) Date of Patent: Mar. 31, 2020

(54) MICRONEEDLE

(71) Applicant: TOPPAN PRINTING CO., LTD., Taito-ku (JP)

(72) Inventor: Yoshihiro Kodama, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

(21) Appl. No.: 15/673,739

(22) Filed: Aug. 10, 2017

(65) Prior Publication Data

US 2017/0333691 A1 Nov. 23, 2017

Related U.S. Application Data

(63) Continuation of application No. PCT/JP2016/053996, filed on Feb. 10, 2016.

(30) Foreign Application Priority Data

Feb. 16, 2015 (JP) .................................. 2015-027863

(51) Int. Cl.
*A61M 37/00* (2006.01)
*A61M 5/46* (2006.01)
(Continued)

(52) U.S. Cl.
CPC ....... *A61M 37/0015* (2013.01); *B29C 45/261* (2013.01); *B29C 45/2628* (2013.01);
(Continued)

(58) Field of Classification Search
CPC . A61B 2010/008; A61B 5/685; A61B 17/205; A61M 2037/0053; A61M 2037/0023
See application file for complete search history.

(56) References Cited

U.S. PATENT DOCUMENTS 6,132,755 A * 10/2000 Eicher ................. A61M 31/002
424/427
7,347,835 B2 3/2008 Maenosono et al.
(Continued)

FOREIGN PATENT DOCUMENTS

DE 102008052749 A1 * 5/2010 ........ A61M 37/0015
EP 2 589 397 A1 5/2013
(Continued)

OTHER PUBLICATIONS

Extended European Search Report dated Aug. 8, 2018 in Patent Application No. 16752382.8, 9 pages.
(Continued)

*Primary Examiner* — Laura A Bouchelle
*Assistant Examiner* — Mark A Igel
(74) *Attorney, Agent, or Firm* — Oblon, McClelland, Maier & Neustadt, L.L.P.

(57) ABSTRACT

A microneedle including a projection having a through hole formed in the projection in a direction that the projection extends, and a tubular member having an end surface configured to support the projection when the end surface is pressed against a skin and a fluid is supplied through the through hole of the projection to the skin. The projection has a length H along the direction that the projection extends and the supporting surface has an area S such that a ratio of S/H is in a range of from 2.1 to 10.5.

20 Claims, 8 Drawing Sheets

(51) Int. Cl.
*B29C 45/26* (2006.01)
*B29L 31/00* (2006.01)
*B29C 45/36* (2006.01)
*B29C 45/00* (2006.01)
*B29K 101/12* (2006.01)

(52) U.S. Cl.
CPC ......... *A61M 5/46* (2013.01); *A61M 2037/003* (2013.01); *A61M 2037/0023* (2013.01); *A61M 2037/0053* (2013.01); *B29C 45/36* (2013.01); *B29C 2045/0094* (2013.01); *B29K 2101/12* (2013.01); *B29L 2031/756* (2013.01); *B29L 2031/7544* (2013.01)

(56) References Cited

U.S. PATENT DOCUMENTS

| | | | |
|---|---|---|---|
| 7,842,008 B2 | 11/2010 | Clarke et al. | |
| 8,419,684 B2 | 4/2013 | Clarke et al. | |
| 9,452,257 B2 | 9/2016 | Clarke et al. | |
| 2003/0009113 A1* | 1/2003 | Olson | A61B 5/14532 600/573 |
| 2003/0199822 A1* | 10/2003 | Alchas | A61M 5/3202 604/117 |
| 2006/0127465 A1 | 6/2006 | Maenosono et al. | |
| 2009/0234288 A1 | 9/2009 | Fischer | |
| 2011/0237925 A1* | 9/2011 | Yue | A61K 9/0021 600/392 |
| 2011/0264048 A1 | 10/2011 | O'Dea et al. | |
| 2011/0295230 A1 | 12/2011 | O'Dea et al. | |
| 2012/0089117 A1* | 4/2012 | Junginger | A61B 17/205 604/506 |
| 2012/0123387 A1 | 5/2012 | Gonzalez et al. | |
| 2013/0110053 A1* | 5/2013 | Yoshino | A61M 5/2425 604/201 |
| 2014/0257188 A1* | 9/2014 | Kendall | A61B 17/205 604/173 |
| 2016/0151617 A1* | 6/2016 | Berry | A61B 5/150022 600/576 |

FOREIGN PATENT DOCUMENTS

| | | |
|---|---|---|
| JP | 2005-021677 A | 1/2005 |
| JP | 2009-039171 A | 2/2009 |
| JP | 2009-516572 A | 4/2009 |
| JP | 2011-513036 A | 4/2011 |
| JP | 2013-500773 A | 1/2013 |

OTHER PUBLICATIONS

International Search Report dated May 17, 2016 in PCT/JP2016/053996, filed Feb. 10, 2016.

\* cited by examiner

MICRONEEDLE

CROSS-REFERENCE TO RELATED APPLICATIONS

The present application is a continuation of International Application No. PCT/JP2016/053996, filed Feb. 10, 2016, which is based upon and claims the benefits of priority to Japanese Application No. 2015-027863, filed Feb. 16, 2015. The entire contents of these applications are incorporated herein by reference.

BACKGROUND OF THE INVENTION

Field of the Invention

The present invention relates to a microneedle for percutaneous administration.

Discussion of the Background

Drug administration using a microneedle is known as a method for administration of drugs such as vaccine into the body (for example, see PTL 1). The microneedle includes projections having a needle-shaped formed on the surface of a substrate. In the administration method using a microneedle, the substrate is pressed against the skin so that the projection punctures the skin to form a hole, through which a drug is delivered into the skin. Since the projection has a length that does not reach nerve cells in the dermis layer of the skin, the administration method using a microneedle reduces pain caused by forming the hole on the skin compared with an administration method using an injection needle. Further, in the administration method using a microneedle, a drug is administered into the skin, which is abundant in antigen-presenting cells. Accordingly, the dose of the drug may be reduced compared with a subcutaneous injection using the injection needle.

According to a drug administration method using a microneedle, the method uses a microneedle having a through hole that penetrates a substrate and a projection in an extending direction of the projection. Through this through hole, a liquid drug is administered into the skin. Administration of a liquid drug using the above method typically uses a device such as an applicator that assists puncturing of the skin by the projection and supplying the liquid drug into the through hole.

For example, in order to prevent part of a liquid drug from being leaked onto the skin surface or leaked subcutaneously during drug administration, a device provided with a limiter that controls insertion depth of the projection into the skin and a stabilizer that prevents deformation of the skin around the projection has been proposed (see PTL 2). Further, a device in which a spring is assembled around a microneedle, and a biasing force of puncturing the skin is applied to the projection by the spring force, so that the projection is prevented from being detached from the skin during drug administration has been proposed as an example (see PTL 3).

PTL 1: JP-2005-021677 A
PTL 2: JP-2009-516572 A
PTL 3: JP-2013-500773 A

SUMMARY OF THE INVENTION

According to an aspect of the present invention, a microneedle includes a projection having a through hole formed in the projection in a direction that the projection extends, and a tubular member having an end surface configured to support the projection when the end surface is pressed against a skin and a fluid is supplied through the through hole of the projection to the skin. The projection has a length H along the direction that the projection extends and the supporting surface has an area S such that a ratio of S/H is in a range of from 2.1 to 10.5.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
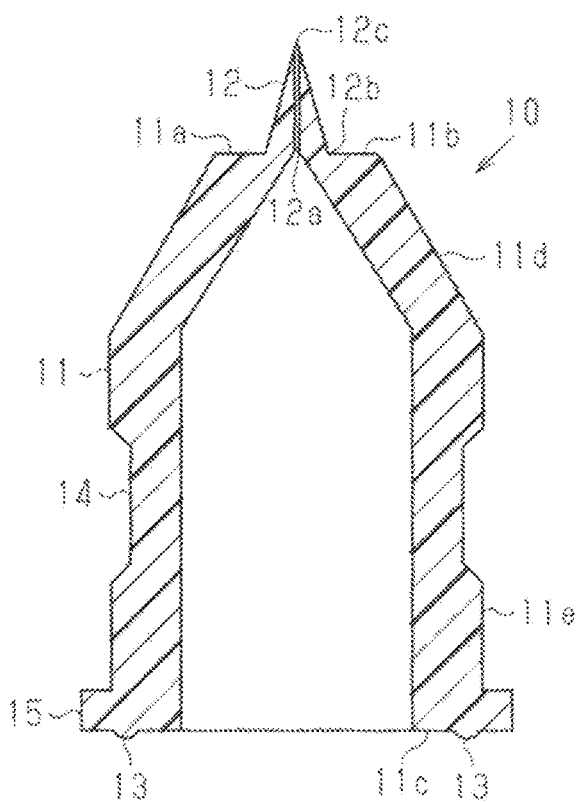
FIG. 1 is a cross sectional view which illustrates a cross sectional structure of a microneedle according to an embodiment of the present invention.

The embodiments will now be described with reference to the accompanying drawings, wherein like reference numerals designate corresponding or identical elements throughout the various drawings.

With reference to FIGS. 1 to 12, an embodiment of a microneedle of the present invention will be described. The following describes a configuration and an operation of the microneedle and a method for manufacturing the microneedle.

Overall Configuration of Microneedle

As shown in FIG. 1, a microneedle 10 includes one tubular member 11 and one projection 12 for puncturing the skin. The projection 12 includes a through hole 12a, which penetrates the projection 12 along a direction where the projection 12 extends. The tubular member 11 has a supporting surface 11a as an end face which is a flat surface for supporting the projection 12, and is pressed against the skin. The tubular member 11 is configured to supply a fluid to the through hole 12a of the projection 12. The fluid supplied to the though hole 12a is, for example, a liquid drug which is a drug in the form of liquid.

The tubular member 11 includes a tube distal end 11b having the supporting surface 11a, and a tube proximal end 11c opposite to the tube distal end 11b in a direction in which the tubular member 11 extends. The length of the tubular member 11 is equal to or longer than the length of the projection 12 in the direction in which the tubular member 11 extends.

Although the supporting surface 11a is in a circular shape, it may be in a polygonal shape. Further, the supporting surface 11a is preferably in a symmetric shape. The configuration in which the supporting surface 11a is in a symmetric shape, and the projection 12 protrudes from the center of the supporting surface 11a is preferable in that the supporting surface 11a is kept horizontal relative to the skin when the projection 12 is pierced.

The tubular member 11 is made up of a distal tubular member 11d including the tube distal end 11b, and a proximal tubular member 11e including the tube proximal end 11c. The distal tubular member 11d is in a cone shape, while the proximal tubular portion 11e is in a cylindrical shape. That is, the tubular member 11 has a tapered shape toward the supporting surface 11a.

The tubular member 11 may be a cylindrical or a cone shape from the tube proximal end 11c to the tube distal end 11b. Further, the tubular member 11 may be a shape other than a cylinder and a cone shape, for example, a prism or a pyramid shape, or alternatively, may be a shape formed of a combination of two or more shapes of a cylinder, a cone, a prism and a pyramid shape.

The inner peripheral surface of the proximal tubular member 11e and the distal tubular member 11d of the tubular member 11 is, for example, a substantially cylindrical shape and a triangular pyramid surface, respectively. In the tubular member 11, it is preferred that an inner diameter of the proximal tubular member 11e gradually decreases in the direction from the tube proximal end 11c to the tube distal end 11b. Preferably, the inner diameter of the tube proximal end 11c is, for example, 4.3 mm, and gradually decreases from the tube proximal end 11c toward the tube distal end 11b at an inclined angle of 3.43°. Accordingly, the microneedle 10 is fitted into a syringe barrel (sterilized syringe barrel), which conforms to JIS T 3210, at the proximal tubular member 11e.

In the tube proximal end 11c of the tubular member 11, two gate marks 13 are formed on the tube proximal end 11c at an interval in the circumferential direction of the tube proximal end 11c. That is, in the tube proximal end 11c of the tubular member 11, two gate marks 13 are located on the tube proximal end 11c at an interval in the circumferential direction of the tube proximal end 11c. Each of the gate marks 13 is a part in which a gate for injecting resin into a mold is formed when the tubular member 11 and the projection 12 are integrally formed using injection molding. The number of the gate mark 13 formed at the tubular member 11 may be one, or two or more.

On the outer peripheral surface of the tubular member 11, a recess 14 is formed. That is, the outer peripheral surface of the tubular member 11 is provided with the recess 14. The recess 14 is preferably formed on the proximal tubular member 11e, and more preferably, the two recesses 14 are formed on the proximal tubular member 11e at an equal interval in the circumferential direction of the proximal tubular member 11e. That is, the recess 14 is preferably located on the proximal side tubular member 11e, and more preferably, the two recesses 14 are located on the proximal tubular member 11e at an equal interval in the circumferential direction of the proximal tubular member 11e. Since a tool or a human finger for holding the microneedle 10 can fit into the recess 14, the microneedle 10 is easily held by the tool or the human finger compared with a configuration of the microneedle 10 which does not include a recess. Accordingly, the microneedle 10 is easily attached to and removed from a member such as a syringe barrel.

The recess 14 may be formed at the entire circumferential direction of the tubular member 11, or three or more recesses 14 may be formed on the tubular member 11 at an interval in the circumferential direction of the tubular member 11. Further, the recess 14 may be formed on the distal tubular member 11d of the tubular member 11. Alternatively, the tubular member 11 may include a plurality of the recesses 14 different from each other in positions in the extending direction of the tubular member 11. Further, the tubular member 11 may include a plurality of the recesses 14 extending in the extending direction of the tubular member 11, and located on the tubular member 11 at an interval in the circumferential direction of the tubular member 11.

The tubular member 11 includes a flange 15 which outwardly extends from the outer peripheral surface of the tube proximal end 11c. The flange 15 is preferably in the same shape as a flange of a lock type connector which conforms to ISO 594-2. Alternatively, the flange 15 may be in a shape similar to a flange of a lock type connector which conforms to ISO 594-2.

With this configuration, the microneedle 10 can be attached to both a Luer-taper type syringe barrel and a Luer-lock type syringe barrel having a lock type connector.

When attaching the microneedle 10 to the Luer-taper type syringe barrel, operators can attach the microneedle 10 to the syringe barrel by fitting the proximal tubular member 11e to a tip of the syringe barrel. On the other hand, operators can remove the microneedle 10 from the syringe barrel by disengaging the proximal tubular member 11e of the microneedle 10 from the tip of the syringe barrel.

Further, when the microneedle 10 is attached to the Luer-lock type syringe barrel, operators can attach the microneedle 10 to the syringe barrel by rotating the flange 15 of the microneedle 10 along a groove formed in a tip of the syringe barrel in one direction. On the other hand, operators can remove the microneedle 10 from the syringe barrel by rotating the flange 15 of the microneedle 10 along the groove formed in the tip of the syringe barrel in the direction opposite to the one direction.

As described above, according to the microneedle 10 having the flange 15, the microneedle 10 can be attached to and removed from the Luer-lock type syringe barrel.

An injection pressure for intracutaneous injection of a drug solution is relatively higher than that of subcutaneous injection of the drug solution. Therefore, compared with the Luer-taper type connection, a Luer-lock type connection that can withstand a higher pressure load is preferred as a connection of the microneedle 10 with the syringe barrel.

The flange 15 may be formed at part of the circumferential direction of the tube proximal end 11c, or a plurality of the flanges 15 may be formed on the tube proximal end 11c at an interval in the circumferential direction of the tube proximal end 11c.

The projection 12 extends from the supporting surface 11a included in the tube distal end 11b of the tubular member 11 to the opposite side of the tubular member 11. The projection 12 has a projection proximal end 12b connected to the supporting surface 11a and a projection distal end 12c which is an end located away from the supporting surface 11a.

The projection 12 is preferably located at the center including a center of the supporting surface 11a. Further, the projection 12 is preferably shaped to have a thinness and a tip angle sufficient for piercing the skin and a length sufficient for subcutaneous delivery of a liquid drug. That is, the shape of the projection 12 preferably has a cross sectional area which decreases toward the tip.

Although the projection 12 has, for example, a cone shape, it may be a pyramidal shape such as a quadrangular or a triangular pyramid, a cylinder shape and a prism shape. Further, the projection 12 may have two or more different shapes of those described above, or may have an asymmetric shape similar to the shapes included in the above described shapes in the extending direction of the projection 12. Further, the outer peripheral surface of the projection 12 may include a groove, or may be formed by a stepped surface.

The microneedle 10 is preferably an integrally molded product in which the tubular member 11 and the projection 12 are integrally formed of resin, in other words, it is preferred that the microneedle 10 is integrally formed of resin. The forming material of the microneedle 10 is a resin which includes a general-purpose plastic, a medical-grade plastic and a cosmetic-grade plastic and the like. More specifically, the forming material of the microneedle 10 is at least one selected from a group consisting of, for example, polyethylene, polypropylene, polystyrene, polyamide, polycarbonate, a cyclic polyolefin, polylactic acid, polyglycolic acid, polycaprolactone, acryl, urethane resin, aromatic polyether ketone and epoxy resin. Further, the forming material of the microneedle 10 may be a copolymeric material of two or more resin included in the resin group, described above.

Detailed Configuration of Microneedle

Figure 2:
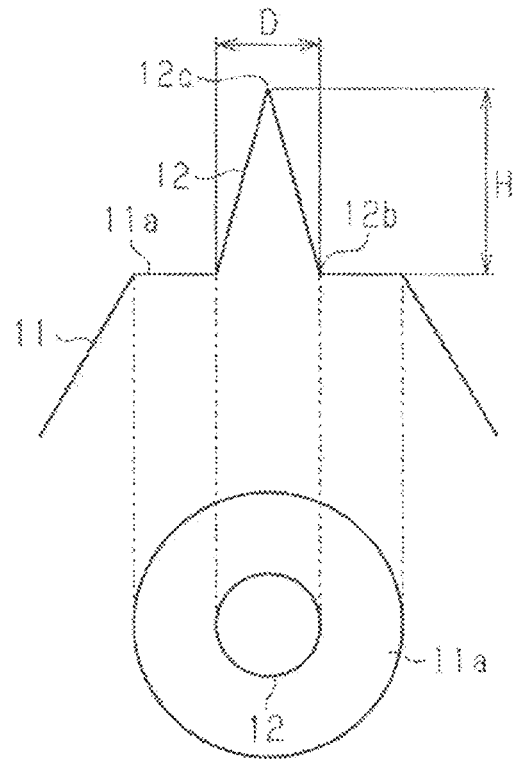
FIG. 2 is a schematic view illustrating a length of a projection and an area of an end face of a tubular member of the microneedle.
Figure 3:
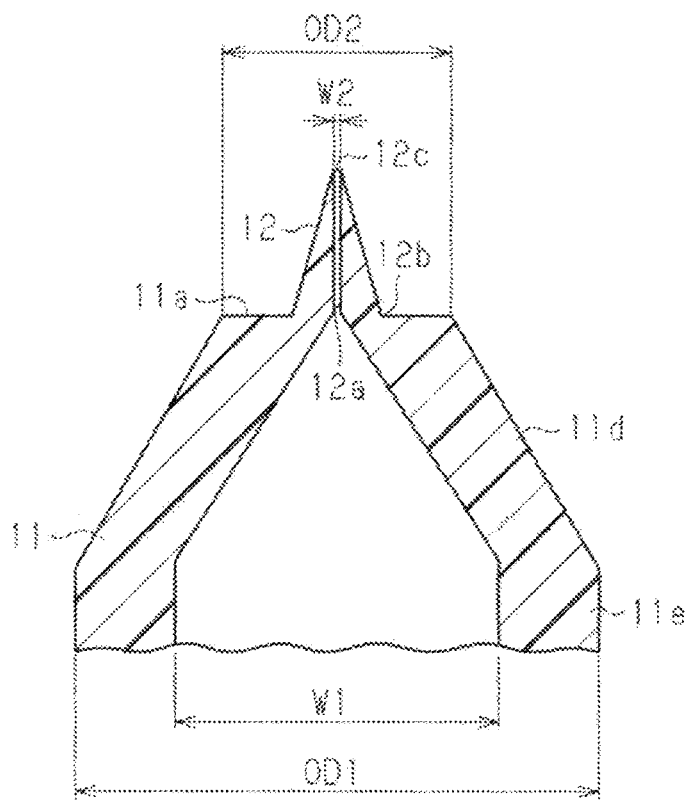
FIG. 3 is a partially enlarged view of a cross sectional structure of the microneedle.

With reference to FIGS. 2 and 3, the detailed configuration of a microneedle will be described. For convenience of explanation of the shape of the microneedle 10, FIG. 2 schematically illustrates the microneedle 10.

As shown in FIG. 2, in the projection 12 has the length H in the extending direction of the projection 12 that is a length from the projection proximal end 12b to the projection distal end 12c. The length H is preferably in such a range that penetrates the stratum corneum, which is the outermost layer of the skin, and does not reach the nerve plexus. That is, the length H of the projection 12 preferably ranges from several hundreds of micrometers to several millimeters, inclusive, for example, from 0.3 mm to 2.5 mm, inclusive, and more preferably, from 0.5 mm to 1.5 mm, inclusive. Further, the width D of the projection 12 in the direction along the supporting surface 11a preferably ranges from several tens of micrometers to several hundreds of micrometers, inclusive.

The area S, an area of the supporting surface 11a, preferably ranges from, for example, 0.5 mm$^2$ or more to 80 mm$^2$ or less, and more preferably ranges from 3 mm$^2$ or more to 13 mm$^2$ or less, and further more preferably ranges from 3 mm$^2$ or more to 7 mm$^2$ or less.

In the projection 12, the ratio of the area S to the length H, that is, the S/H value determined by dividing the area S by the length H is 2.1 or more and 10.5 or less.

As shown in FIG. 3, in the tubular member 11, an outer diameter of the proximal tubular member 11e except for the recess 14, described above, is a proximal outer diameter OD1, and an outer diameter of the supporting surface 11a is an end face outer diameter OD2. An outer diameter of the tubular member 11 gradually decreases from the proximal outer diameter OD1 to the end face outer diameter OD2 at the distal tubular member 11d.

Further, in the tubular member 11, an aperture width of the proximal tubular member 11e is a proximal width W1, and an aperture with of the supporting surface 11a is an end face width W2. The end face width W2 is equal to an inner diameter of the through hole 12a configured with, for example, a cylindrical surface. In the distal tubular member 11, the aperture width of the tubular member 11 gradually decreases from the proximal width W1 to the end face width W2 at the distal tubular member 11d. Accordingly, when a fluid such as a liquid drug is released from the projection 12, the flow of fluid within the tubular member 11 can be laminar rather than turbulent, thereby reducing a resistance generated when the fluid is released.

Operation of Microneedle

Figure 4:
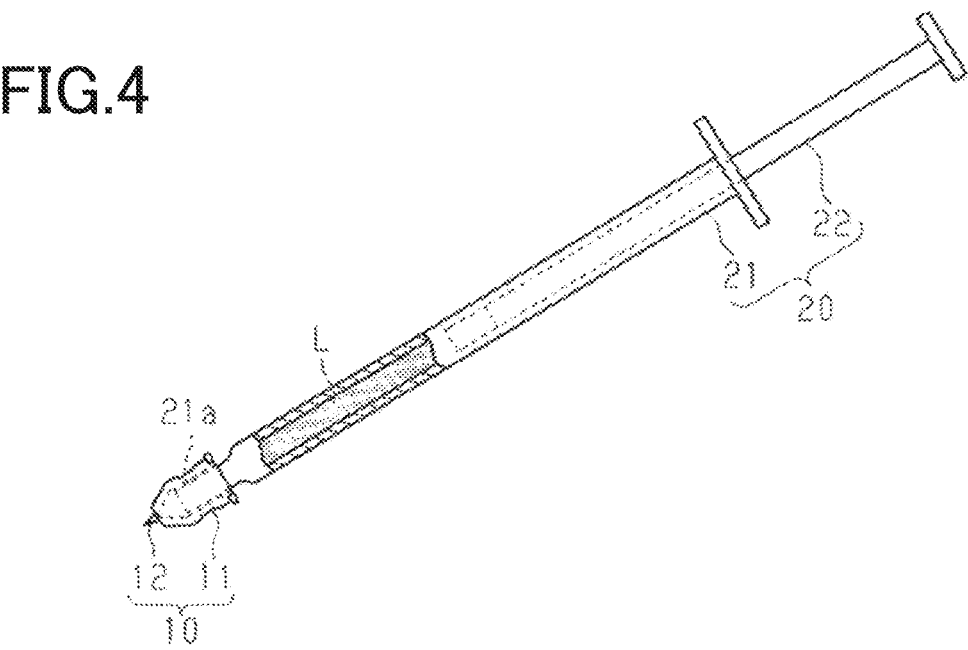
FIG. 4 is a perspective view which illustrates the microneedle attached to a syringe barrel wherein a part of an external cylinder of the syringe barrel is broken away.
Figure 5:
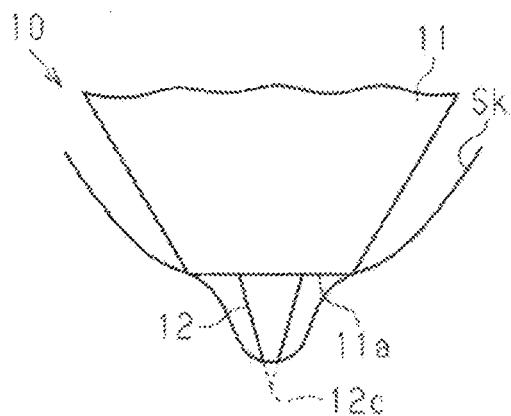
FIG. 5 is an operation view which illustrates an operation of the microneedle.
Figure 6:
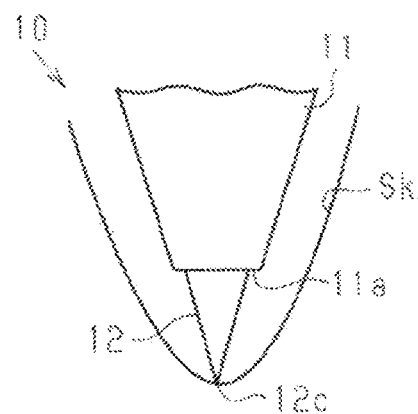
FIG. 6 is an operation view which illustrates an operation of the microneedle.
Figure 7:
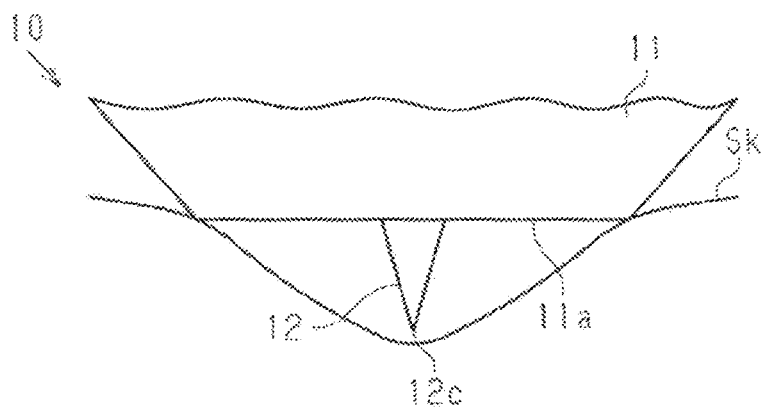
FIG. 7 is an operation view which illustrates an operation of the microneedle.

With reference to FIGS. 4 to 7, an operation of a microneedle will be described. FIG. 4 illustrates the microneedle attached to a Luer-taper type syringe barrel which is one example of a syringe barrel. For convenience of illustration, FIGS. 5 to 7 schematically illustrate the microneedle 10.

As shown in FIG. 4, the microneedle 10 is attached to a cylinder tip 21a included in an external cylinder 21 of a syringe barrel 20 when in use. Then, a plunger 22 is pushed into the microneedle 10 while the projection 12 of the microneedle 10 is pierced into the target for administration of a liquid drug L, for example, human skin. The projection 12 may be pierced into the skin with a puncture load which approximately ranges from 5 N to 100 N. Further, the projection 12 may be pierced into the skin at a puncture speed which ranges between 0.01 mm/s or more, which is the speed of manual operation, and 1000 mm/s or less, which is the speed of puncture assisted by a power source such as a spring. Accordingly, the liquid drug L in the external cylinder 21 is supplied to the tubular member 11 of the microneedle 10, and the liquid drug L in the tubular member 11 is supplied to the through hole 12a of the projection 12, thereby administering the liquid drug L into the skin.

As shown in FIG. 5, when the ratio of the area S of the supporting surface 11a to the length H of the projection 12 is 2.1 or more, a part of a skin Sk surrounding a part to be punctured by the projection is stretched by the supporting surface 11a of the tubular member 11 when the projection 12 of the microneedle 10 is pressed against the skin Sk. Therefore, when the projection 12 is pierced into the skin Sk, deformation of a part of the skin Sk, which is punctured by the projection 12 is prevented by the supporting surface 11a of the tubular member 11. Accordingly, a force applied to the projection distal end 12 is less likely to be distributed due to the deformation of the skin Sk, and as a result, the projection 12 can be easily pierced into the skin.

When the ratio of the area S of the supporting surface 11a to the length H of the projection 12 is 10.5 or less, the depth of a recess of the skin Sk pressed by the supporting surface 11a is likely to be shorter than the length of the projection 12. Accordingly, the projection 12 can be easily pierced into the skin Sk.

On the other hand, as shown in FIG. 6, when the ratio of the area S of the supporting surface 11a to the length H of the projection 12 is less than 2.1, an area of a portion of the supporting surface 11a surrounding the projection 12 is small. Accordingly, when the projection distal end 12c of the projection 12 touches the skin Sk, the microneedle 10 touches the skin Sk only by the projection distal end 12c. Therefore, when the projection distal end 12c touches the skin Sk, and applies a force to the skin Sk, the skin Sk is deformed due to an elasticity of the skin Sk. As a consequence, since the force applied to the projection distal end 12c is distributed due to deformation of the skin Sk, it becomes difficult to pierce the projection 12 into the skin.

As shown in FIG. 7, when the ratio of the area S of the supporting surface 11a to the length H of the projection 12 is more than 10.5, an area of a portion of the supporting surface 11a surrounding the projection 12 is large. Here, when the microneedle 10 is pressed against the skin Sk, a portion of the supporting surface 11a which is apart from the projection 12 is likely to touch the skin Sk because it is located away from a portion in which there is a level difference between the supporting surface 11a and the projection 12.

Accordingly, since the skin Sk is likely to be pressed by the outer edge of the supporting surface 11a, a distance between a part of the skin Sk, which is stretched by the supporting surface 11a and a part of the skin Sk in which the projection distal end 12c is pierced becomes larger. As a result, since a part of the skin Sk, which is stretched by the supporting surface 11a is likely to bend, and the depth of a recess of the skin Sk is likely to be longer than the length of the projection 12, it becomes difficult to pierce the projection 12 into the skin Sk.

When the ratio of the area S of the supporting surface 11a to the length H of the projection 12 is more than 10.5, an area of a part of the skin Sk pressed by the supporting surface 11a becomes large. Accordingly, since a force applied to a tip of the microneedle 10 by pressing microneedle 10 against the skin is distributed into the supporting surface 11a and the projection 12, the force applied to a tip of the projection 12 is unlikely to become large enough to pierce the microneedle 10 into the skin Sk. Therefore, it becomes difficult to pierce the microneedle 10 into the skin. This phenomenon is particularly notable when the puncture speed is 200 mm/s or less, which is relatively low in the range of the puncture speed, described above.

In the microneedle 10 made of resin, it is difficult to sharpen the projection distal end 12c which is a needle tip of the projection 12 compared with a microneedle made of metal. In particular, in the microneedle 10 in which the projection 12 has the through hole 12a, the diameter of the projection 12 needs to be increased by the diameter of the through hole 12a. Accordingly, it is difficult to sharpen the projection distal end 12c. As a consequence, it becomes difficult to pierce the projection distal end 12c into the skin.

In this regard, in the microneedle 10 made of resin, as well, the inventors of the present invention have found that the reliability of piercing the projection 12 having the through hole 12a into the skin can be enhanced by setting the ratio of the length H of the projection 12 to the area S of the supporting surface 11a to be in the above range, considering deformation of the skin, and arrived at the present invention.

Method for Manufacturing Microneedle

With reference to the FIGS. 8 to 10, a method for manufacturing a microneedle will be described. Hereinafter, a method for manufacturing the microneedle 10 using injection molding will be described as an example of a method for manufacturing the microneedle 10.

Figure 8:
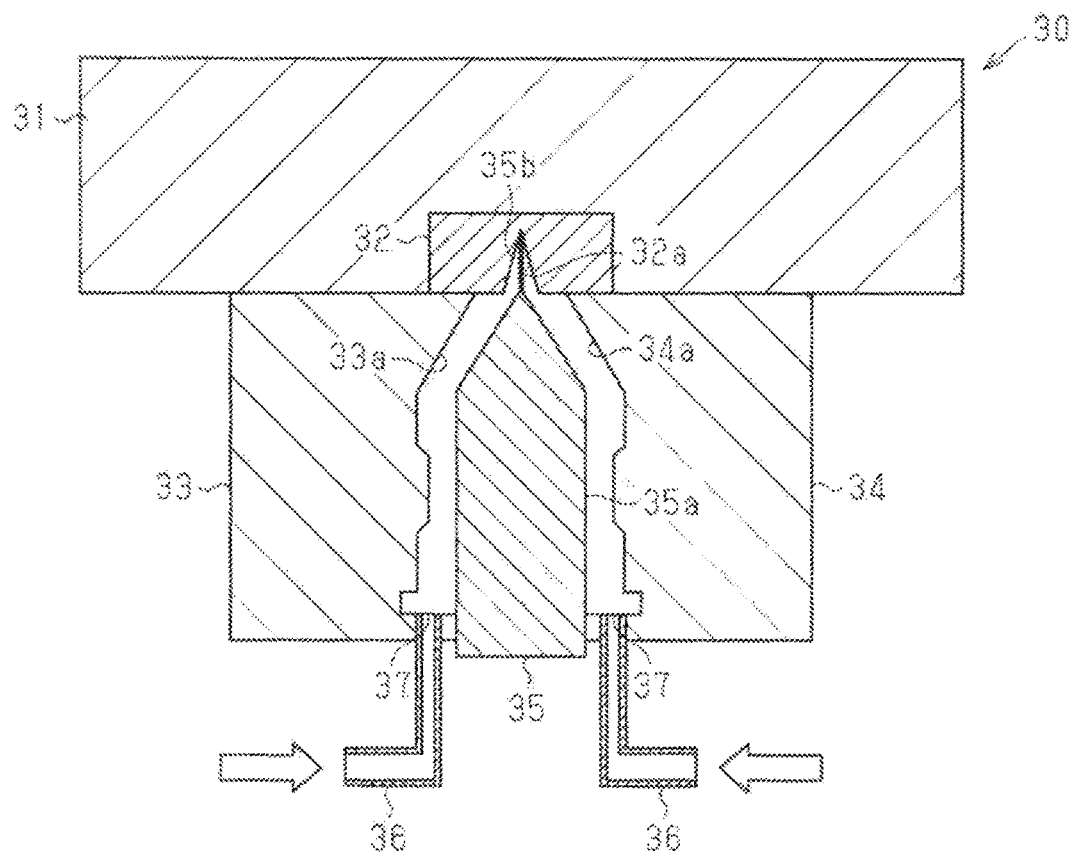
FIG. 8 is a view which illustrates a manufacturing process of the microneedle.

As shown in FIG. 8, an injection mold 30 is provided with a fixed mold 31, an insert 32, a first movable mold 33, a second movable mold 34 and a core pin 35. The injection molder which incorporates the injection mold 30 may be an electric injection molder or a hydraulic injection molder, but preferably an electric and small-sized injection molder.

The insert 32 includes a projection forming groove 32a conforming to the shape of the projection 12 to form the projection 12. The injection mold 30 may not necessarily include the insert 32, and the projection forming groove may be included in the fixed mold 31. However, a configuration of the injection mold 30 having the insert is preferable in that the shape of the projection 12 formed by the insert 32 can be varied by changing the insert 32. The insert 32 may have a configuration in which air remaining in the insert 32 is released to outside the insert 32 when resin is injected into the insert 32.

The first movable mold 33 is a mold that can change the position of the first movable mold 33 relative to the fixed mold 31. The first movable mold 33 includes a cylinder forming groove 33a conforming to one of the shapes of the tubular member 11 divided into two in the circumferential direction of the tubular member 11 to form the tubular member 11. The second movable mold 34 is a mold in which the position of the second movable mold 34 relative to the fixed mold 31 can be varied similar to the first movable mold 33. The second movable mold 34 includes a cylinder forming groove 34a conforming to the other shape of the tubular member 11 divided into two in the circumferential direction of the tubular member 11, that is, a groove conforming to a portion different from the groove of the first movable mold 33 to form the tubular member 11.

The position of the first movable mold 33 and the second movable mold 34 relative to the fixed mold 31 may be varied so as to form the recess 14 which is an undercut portion. Further, the first movable mold 33 and the second movable mold 34 may have an angular pin, an oil-hydraulic mechanism or a pneumatic mechanism as a mechanism for changing the position relative to the fixed mold 31, or may have a spring or like for supporting the operation of these mechanisms.

A core pin 35 is provided with a main body 35a and a tip portion 35b. In the microneedle 10, the main body 35a is a portion for forming an inner peripheral surface of the tubular member 11, and the tip portion 35b is a portion for forming the through hole 12a of the projection 12.

The fixed mold 31, the insert 32, the first movable mold 33, the second movable mold 34 and the core pin 35 that constitute the injection mold 30 may be a combination of plural components.

As described above, in the microneedle 10, it is preferred that the proximal tubular member 11e fitted into the cylinder tip 21a of the external cylinder 21 included in the syringe barrel 20 have an inner diameter larger than the outer diameter of the cylinder tip 21a. On the other hand, in order to prevent difficulty in administrating a liquid drug L to the target when the liquid drug L is contained in the microneedle 10, an aperture width of the distal tubular member 11d connected to the projection 12 preferably has the same inner diameter as that of the through hole 12a of the projection 12.

However, in the extending direction of the tubular member 11, as a portion having an aperture width which has the same inner diameter as the through hole 12a of the projection 12 increases, the tip portion 35b used for forming a fine-width aperture of the microneedle 10 increases in length. As a result, the tip portion 35b can be easily broken, and become difficult to detach from the microneedle 10. Accordingly, the shape accuracy of the inner peripheral surface of the microneedle 10 is likely to be decreased.

In this regard, according to a configuration in which the aperture width of the tubular member 11 gradually decreases from the proximal width W1 to the end face width W2 at the distal tubular member 11d, the tip portion 35b can be decreased in length, thereby preventing the tip portion 35b from being broken, and enhancing the shape accuracy of the inner peripheral surface of the microneedle 10.

Each of the first movable mold 33 and the second movable mold 34 include a runner 36.

In each of the movable mold, a gate 37 to which runners 36 are connected is formed on the position corresponding the tube proximal end 11c of the microneedle 10. Since two gates 37 are formed, a flow of resin in the injection mold 30 can be more strictly controlled compared with the configuration in which only one gate is formed. The gate 37 may be any one of a pinpoint gate, a film gate, a valve gate or the like.

The injection mold 30 may be a hot runner type mold which includes a heater heating the runner 36. According to the hot runner type mold, since a resin injected into the injection mold 30 is kept in a molten state just before entering the gate 37, formation of the runner formed by conforming to the shape of the runner 36 can be prevented.

When manufacturing the microneedle 10, molten resin is injected from the injection molder to the injection mold 30. Accordingly, resin is injected into a space defined by the insert 32, the first movable mold 33, the second movable mold 34 and the core pin 35 through the runners 36 and the gates 37.

Figure 9:
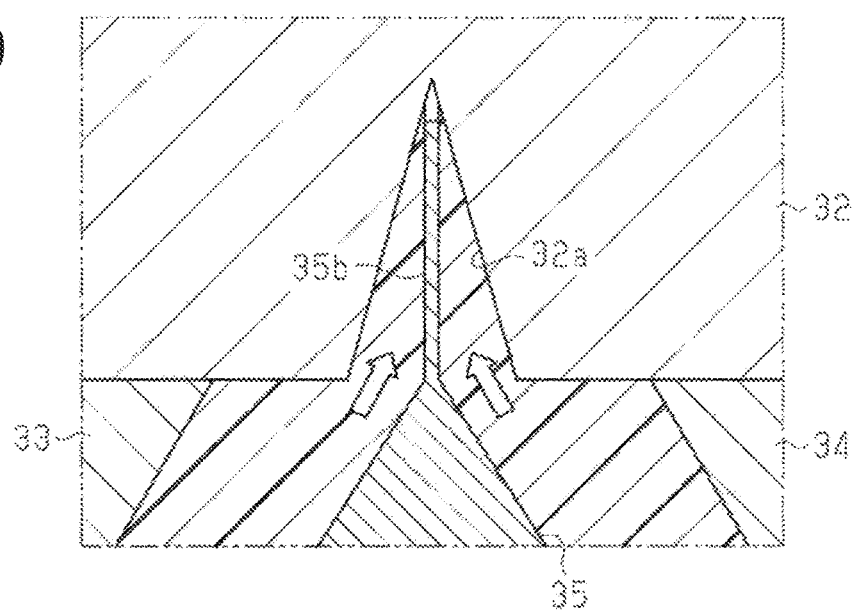
FIG. 9 is a view which illustrates a manufacturing process of the microneedle.

Here, as shown in FIG. 9, a tip of the tip portion 35b of the core pin 35, which is an end located away from the main body 35a, is not in contact with the projection forming groove 32a formed in the insert 32. Accordingly, the tip portion 35b is prevented from being deformed or broken as the tip portion 35b is in the contact with the insert 32.

On the other hand, the gate 37 is formed at the portion corresponding to the tube proximal end 11c in each of the movable molds. Accordingly, the distance from the gate 37 to the projection forming groove 32a becomes large enough to reliably inject resin into the projection forming groove 32a, and to inject resin toward the bottom of the projection forming groove 32a, passing the tip of the tip portion 35b of the core pin 35. Hence, the shape of the microneedle 10, especially the shape of the projection 12, conforms to the injection mold 30 with higher precision.

Figure 10:
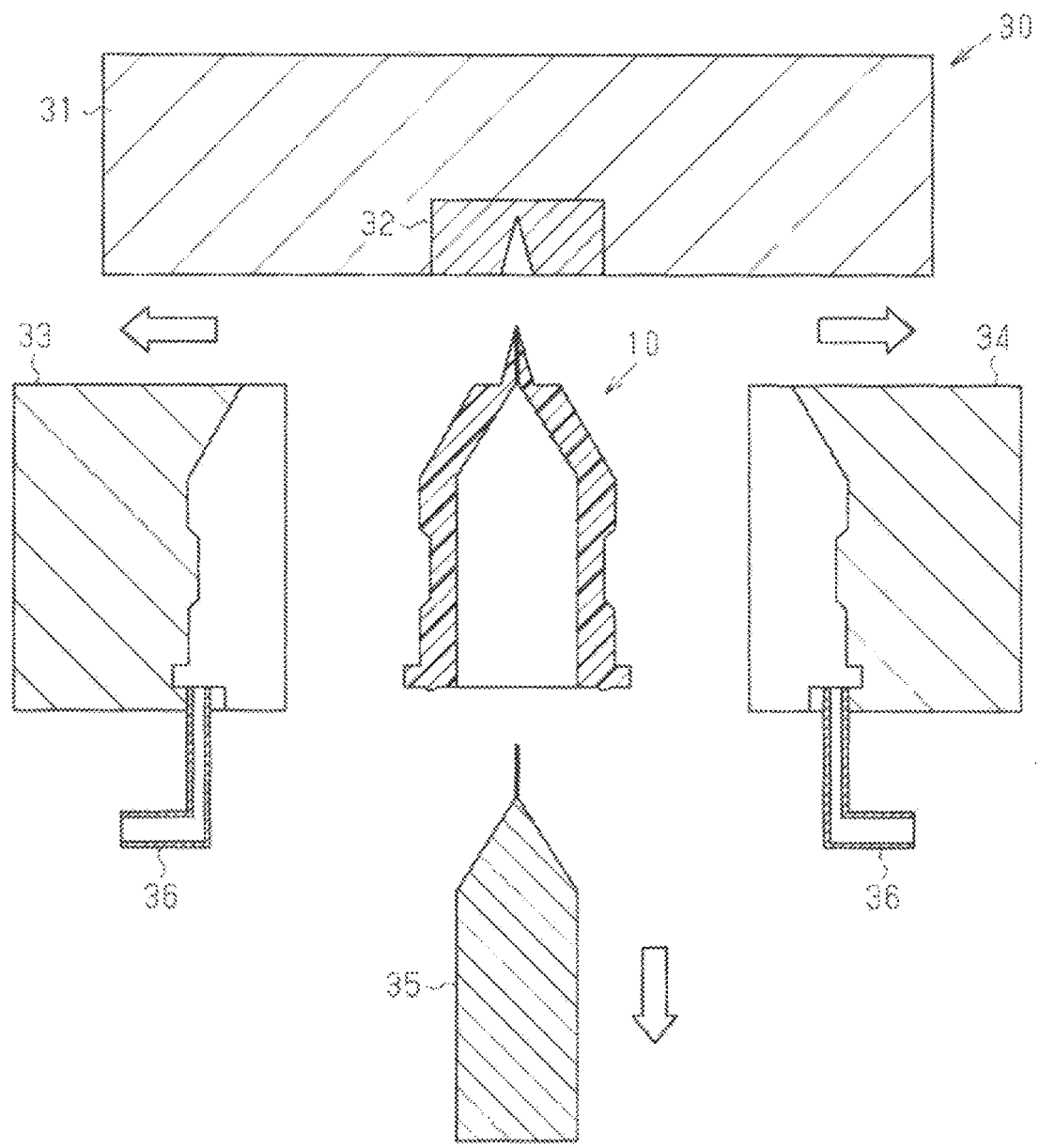
FIG. 10 is a view which illustrates a manufacturing process of the microneedle.

As shown in FIG. 10, when resin injected into the injection mold 30 is cured, the microneedle 10 is removed from the injection mold 30 by displacing the first movable mold 33, the second movable mold 34 and the core pin 35 relative to the fixed mold 31. The injection mold 30 may include an ejector pin for pushing the molded microneedle 10 out of the injection mold 30.

As described above, at the distal tubular member 11d of the microneedle 10, the outer diameter gradually decreases in the direction from the tube proximal end 11c to the tube distal end 11b. Accordingly, while the area S of the supporting surface 11a is set to be in the preferable size range described above, the outer diameter of the portion closer to the tube proximal end 11c than to the supporting surface 11a becomes larger than to the supporting surface 11a. That is, a cross section perpendicular to the extending direction of the distal tubular member 11d gradually increases from the supporting surface 11a in the direction from the tube distal end 11b to the tube proximal end 11c. Thus, the tubular member 11 gradually becomes thicker toward the end further from the supporting surface 11a which requires fine processing. Therefore, when manufacturing the microneedle 10, a portion corresponding to a portion of the microneedle 10 except for the projection 12 is firstly filled with resin in the injection mold 30, and then a portion corresponding to the projection 12 is finally filled with resin in the injection mold 30, thereby enhancing the filling of resin into the injection mold 30 and the formability of the microneedle 10.

The distal tubular member 11d of the tubular member 11 is in a tapered shape, thereby being easily removed from the injection mold 30 compared with the configuration in which the distal tubular member has a constant outer diameter. Therefore, the shape of the tubular member 11 conforms to the mold of the microneedle 10 with higher precision.

The injection mold 30 may be designed to be incorporated in a general-purpose mold base. The mold base may have a two-plate structure, a three-plate structure or the like. Further, processing for incorporating a water channel for cooling, or a heater for heating may be applied to the mold base. The forming material of the mold base may be, for example, a carbon steel. Further, the injection mold 30 may be disposed in a mold clamped in advance.

EXAMPLE

Method for Manufacturing Microneedle

A fixed mold and two removable molds and a mold base incorporating a core pin were provided as an injection mold. In the fixed mold, an insert including a projection forming groove was incorporated. In a main body of the core pin, a portion corresponding to a proximal tubular member of a tubular member is set to have a cylinder shape, and a portion corresponding to a distal tubular member of the tubular member is set to have a pyramid shape, A tip portion of the core pin is set to be a cylinder shape with a diameter of 100 µm. Further, in each of two removable molds, a gate was formed at a portion corresponding to a tube proximal end.

Figure 11:
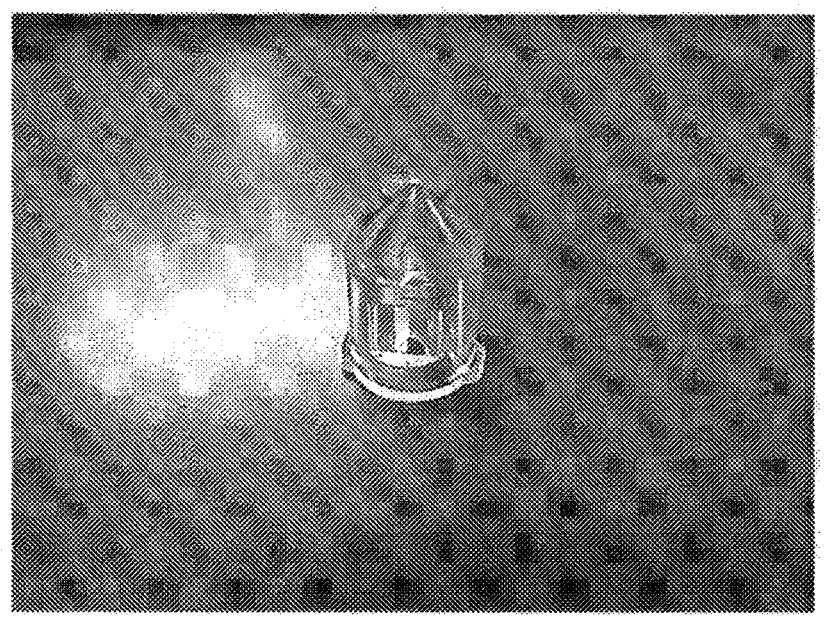
FIG. 11 is an image obtained by picking up an image of an entire microneedle of an embodiment.

The injection mold was incorporated into an all-electric injection molder (manufactured by Sumitomo Heavy Industries, Ltd., SE18DU) and polycarbonate which was heated at a temperature of 290° C. was injected into the injection mold at an injection speed of 50 mm/sec, followed by heating the injection mold for a period of 10 seconds. Between the two gates, a runner was designed so that a timing of injecting resin differs by only 0.1 seconds. The molded product was taken out from the injection mold, followed by removing the runners to thereby obtain a microneedle having a tubular member and a projection, as shown in FIG. 11.

Figure 12:
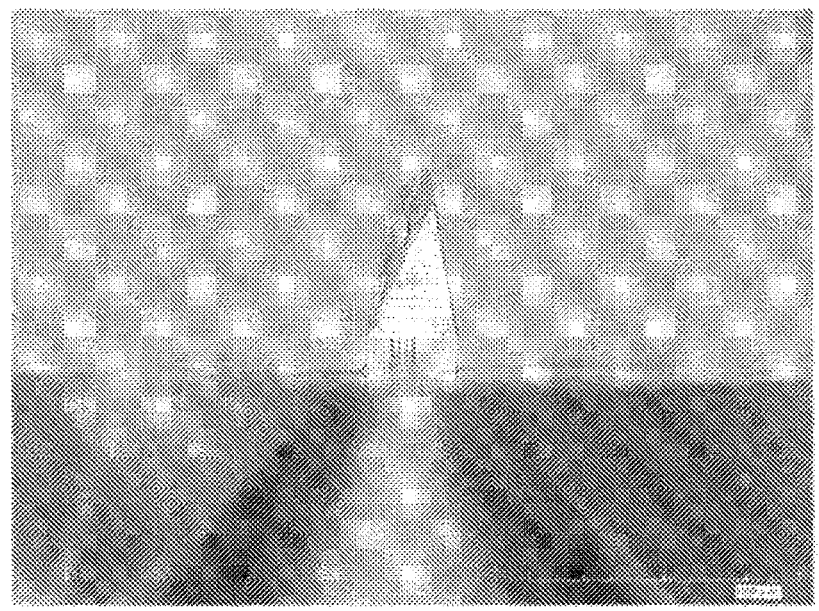
FIG. 12 is an image obtained by picking up an image enlarged by a microscope of a projection included in a microneedle of an embodiment.

As shown in FIG. 12, observing the microneedle using a microscope, it was observed that a through hole which penetrates the microneedle from a tube proximal end to a side surface of the projection along the extending direction of the projection is formed. Further, it was observed that the diameter of the through hole around the tip portion of the projection was 50 µm. Furthermore, it was observed that, when a tip of a syringe barrel was inserted into the tubular member of the microneedle and water was discharged from the microneedle, the water was discharged from the projection without being leaked from other portions.

Shape of Microneedle

Microneedles provided with a tubular member which is in a cylindrical shape at the proximal end and in a cone shape at the distal end, and having a diameter of the tubular member of 1 mm, 2 mm, 3 mm, 4 mm or 10 mm at an end surface were manufactured. Hereinafter, when the end surface has a 1 mm diameter, an area S of the end surface is 0.8 mm$^2$, and when the end surface has a 2 mm diameter, the area S of the end surface is 3 mm$^2$, and when the end surface has a 3 mm diameter, the area S of the end surface is 7 mm$^2$. Furthermore, when the end surface has a 4 mm diameter, the area S of the end surface is 13 mm$^2$, and when the end surface has a 10 mm diameter, the area of the end surface is 79 mm$^2$. Further, in the microneedle which has a 10 mm diameter of the tubular member at the end surface and a cone shape at the distal tubular member of the tubular member, a portion having a regular quadrangular pyramid shape was cut out from the distal tubular member, thereby manufacturing a microneedle provided with the tubular member which has a cylindrical shape at the proximal end and a regular quadrangular pyramid shape at the distal end, and this had sides 7 mm in length on the end surface, and an area S at the end surface of 49 mm$^2$.

Then, six microneedles different from each other in the area S of the end surface in which the length H of the projection 12 was 0.5 mm, 0.7 mm, 1 mm 1.2 mm or 1.5 mm were manufactured.

Drug Administration Test

The microneedle was attached to the syringe barrel, followed by assembling a syringe made up of the microneedle and the syringe barrel to a dedicated tool for a syringe to apply an arbitrary load and puncture rate.

The skin of 20 weeks-old Wistar rat was prepared as a target for administration, followed by removing the hair of the Wistar rat using a hair clipper. Further, blue-dyed saline was prepared as a liquid drug to be administrated. The projection of the microneedle was pierced into the skin of the rat using the tool with load of 30 N at the puncture rate of 100 mm/s. Then, after the puncture position was stabilized, 50 μl blue-dyed saline was injected to the skin by pushing the plunger in the syringe barrel. When a scale on an external cylinder showed that a moving amount of the liquid drug was 50 μl, the plunger was released. The state of showing the moving amount of the liquid drug of 50 μl was maintained for 5 minutes, and then the microneedle was removed from the rat skin. At this time, no leakage of the injected liquid drug onto the skin surface was found.

Method for Evaluation

The back surface of the rat skin was observed in a state of being exposed to transmitted light. If it was found that the liquid drug was injected into the rat skin, the projection of the microneedle was determined to be pierced into the rat skin. On the other hand, if it was not found that the liquid drug was injected into the rat skin, the projection of the microneedle was not determined to be pierced into the rat skin.

Evaluation Result

With reference to Table 1 shown below, results of evaluating whether the microneedle was pierced into the skin will be described. In Table 1, the symbol o is used to denote that the microneedle was determined to be pierced into the skin, and the symbol x denotes that the microneedle was not determined to be pierced into the skin.

TABLE 1

| | | Area S/Length H (o x · ratio) | | | | | | | | | | |
|---|---|---|---|---|---|---|---|---|---|---|---|---|
| | | Area S (mm$^2$) | | | | | | | | | | |
| | | 0.8 | | 3 | | 7 | | 13 | | 49 | | 79 |
| Length H (mm) | 0.5 | x | 1.6 | o | 6.3 | x | 14.1 | x | 25.1 | x | 98.0 | x | 158 |
| | 0.7 | x | 1.1 | o | 4.5 | o | 10.1 | x | 18.0 | x | 70.0 | x | 113 |
| | 1 | x | 0.8 | o | 3.1 | o | 7.1 | x | 12.6 | x | 49.0 | x | 79.0 |
| | 1.2 | x | 0.7 | o | 2.6 | o | 5.9 | o | 10.5 | x | 40.8 | x | 65.8 |
| | 1.5 | x | 0.5 | o | 2.1 | o | 4.7 | o | 8.4 | x | 32.7 | x | 52.7 |

As shown in Table 1, when the area S of the end surface was 0.8 mm$^2$, the projections of the microneedles having the length H of 0.5 mm, 0.7 mm, 1 mm, 1.2 mm or 1.5 mm were not found to be pierced into the skin. That is, the projection was found not to be pierced into the skin when the ratio of the area S to the length H of the projection was 0.5 or more and 1.6 or less.

When the area S of the end surface was 3 mm$^2$, the projections of the microneedles having the length H of 0.5 mm, 0.7 mm, 1 mm, 1.2 mm or 1.5 mm were found to be pierced into the skin. That is, the projections were found to be pierced into the skin when the ratio of the area S to the length H of the projection was 2.1 or more and 6.3 or less.

When the area S of the end surface was 7 mm$^2$, the projections of the microneedles having the length H of 0.7 mm, 1 mm, 1.2 mm, or 1.5 mm were found to be pierced into the skin. On the other hand, a projection of a microneedle having the length H of 0.5 mm was found not to be pierced into the skin. That is, it was found that when the ratio of the area S to the length H of the projection was 4.7 or more and 10.1 or less, the projection was pierced into the skin, while when the ratio of the area S to the length H of the projection was 14.1, the projection was not pierced into the skin.

When the area S of the end surface was 13 mm$^2$, the projections of the microneedles having the length H of 1.2 mm, or 1.5 mm were found to be pierced into the skin. On the other hand, the projections of the microneedles having the length H of 0.5 mm, 0.7 mm or 1 mm were found not to be pierced into the skin. That is, it was found that when the ratio of the area S to the length H of the projection was 8.4 or more and 10.5 or less, the projection was found to be pierced into the skin, while when the ratio of the area S to the length H of the projection is 12.6 or more and 25.1 or less, the projection was found not to be pierced into the skin.

When the area S of the end surface was 49 mm$^2$ and when the area S of the end surface was 79 mm$^2$, projections of the microneedles having the length H of 0.5 mm, 0.7 mm, 1 mm, 1.2 mm and 1.5 mm were not found to be pierced into the skin. That is, when the ratio of the area S to the length H of the projection was 32.7 or more and 158 or less, the projections were found not to be pierced into the skin.

Accordingly, when the ratio of the area S of the end surface to the length H of the projection was 2.1 or more and 10.5 or less, the projection was observed to be pierced into the skin.

As described above, according to an embodiment of the microneedle, the following effects can be obtained.

(1) Since the ratio of the area S of the supporting surface 11a to the length H of the projection 12 is 2.1 or more and 10.5 or less, the projection 12 can be easily pierced into the skin.

(2) Since the gates 37 are formed at the portion corresponding to the tube proximal end 11c of the injection mold 30, the shape of the microneedle, especially the shape of the projection 12, conforms to the injection mold 30 with high precision.

(3) Since a tool or a human finger for holding the microneedle 10 can fit into the recess 14, the microneedle 10 having the recess can be easily held by the tool or the human finger compared with the configuration of a microneedle which does not include the recess.

(4) Since the tubular member 11 gradually becomes thicker toward the end further from the supporting surface 11a which requires fine resin processing, resin filling into the injection mold 30 can be improved. As a result, formability of the microneedle 10 can be enhanced.

(5) Since the microneedle 10 includes the flange 15, the microneedle 10 can be attached to and removed from a Luer-lock type syringe barrel.

The embodiment described above may be appropriately modified as below.

The tubular member 11 may not necessarily include the flange 15. With this configuration, effects similar to the above (1) to (4) are also achieved. Further, according to the configuration in which the tubular member 11 includes the recess 14, the microneedle 10 can be easily attached to and removed from the syringe barrel 20 by using the recess 14.

The tubular member 11 may not necessarily have a tapered shape toward the supporting surface 11a, but may have the same thickness in the entire extending direction of the tubular member 11. With this configuration, the effects similar to the above (1) to (3), and (5) are also achieved.

The tubular member 11 may not necessarily include the recess 14. In this configuration as well, the effects similar to the above (1), (2), (4) and (5) are also achieved. Further, according to the configuration in which the tubular member 11 includes the flange 15, the microneedle 10 can be attached to and removed from the Luer-taper type syringe barrel 20 by holding the flange 15. This exhibits high workability of attaching and removing the microneedle 10.

The portion in which the gates 37 are formed is not limited to the portion corresponding to the tube proximal end 11c, but may be the following portion. That is, the gates 37 may be formed at the portion closer to the tube proximal end 11c than to the center of the tubular member 11 in the extending direction of the tubular member 11. In this configuration as well, the effect similar to the above (2) is also achieved. Further, in the microneedle 10 formed by such an injection mold 30, the gate marks 13 are formed at the portion closer to the tube proximal end 11c than to the center of the tubular member 11 in the extending direction of the tubular member 11. That is, the gate marks 13 are located at the portion closer to the tube proximal end 11c than to the center of the tubular member 11 in the extending direction of the tubular member 11.

In the injection mold 30, the gates 37 may be formed at the portion corresponding to the portion located between the center of the tubular member 11 and the tube distal end 11b, or at the portion corresponding to the projection 12 in the extending direction of the tubular member 11. In other words, the gates 37 may be formed at the any portion of the microneedle 10 in the injection mold 30 as long as molding of the microneedle 10 having the tubular member 11 and the projection 12 can be achieved.

Other than the above injection molding, the method for manufacturing the microneedle 10 may include other molding methods combining, for example, imprinting, hot embossing, extrusion molding and casting.

The microneedle 10 may not necessarily be formed integrally. For example, the microneedle 10 may be formed by separately forming the tubular member 11 and the projection 12, followed by connecting them. Alternatively, the microneedle 10 may be formed by forming components corresponding to the microneedle 10 divided into plural components in the circumferential direction or the extending direction of the microneedle 10, followed by connecting the plurality of the components. When the microneedle 10 is formed by a plurality of components, the forming materials may be different between the components.

The inner peripheral surface of the distal tubular member 11d may be formed of a conical surface. In this case, in the tubular member 11, the inner diameter of the proximal tubular member 11e is an inner diameter of the proximal end, and the inner diameter of the supporting surface 11a is an inner diameter of the end surface. The inner diameter of the tubular member 11 may be decreased from the inner diameter of the proximal end to the inner diameter of the end surface, and the inner diameter of the end surface may be equal to that of the through hole 12a.

When the inner peripheral surface of the proximal tubular member 11e is tapered in the direction from the tube proximal end 11c to the tube distal end 11b of the tubular member 11, an aperture width of the distal tubular member 11d may be gradually decreased from the end close to the tube proximal end 11c of the distal tubular member 11d to the supporting surface 11a.

As described above, in the tubular member 11, the proximal tubular member 11e may have a shape other than a cylindrical shape, and the distal tubular member 11d may have a cone shape. In this case, the width of an outer shape of the tubular member 11 may be decreased from the proximal tubular member 11e to the supporting surface 11a in the cross section including the center axis of the tubular member 11, for example. That is, a cross section perpendicular to the extending direction of the tubular member 11 may be gradually decreased from the proximal tubular member 11e to the supporting surface 11a in the extending direction of the tubular member 11.

When the distal tubular member 11d is tapered in the direction from the tube proximal end 11c to the tube distal end 11b of the tubular member 11, the width of the outer shape of the distal tubular member 11d may be decreased from the end close to the tube proximal end 11c of the distal tubular member 11d to the supporting surface 11a.

In the tubular member 11, the aperture width of the distal tubular member 11d may be equal to that of the proximal tubular member 11e, or may be equal to the inner diameter of the though hole 12a formed in the projection 12 in the entire extending direction of the tubular member 11. Alternatively, the aperture width of the distal tubular member 11d may be a certain width between the aperture width of the proximal tubular member 11e and the inner diameter of the though hole 12a in the entire extending direction of the tubular member 11.

Figure 13:
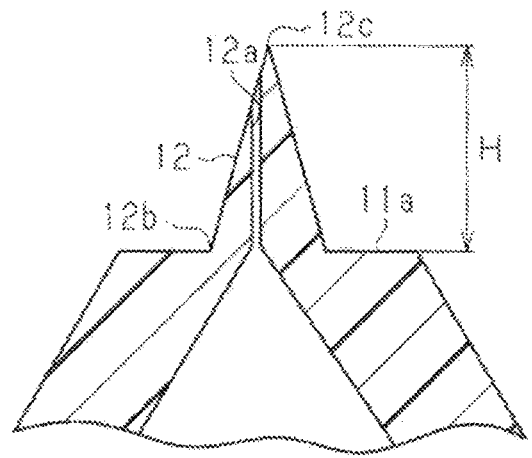
FIG. 13 is a partially enlarged view which illustrates a cross sectional structure of a microneedle in a modified example.

As shown in FIG. 13, the through hole 12a which extends from the projection proximal end 12b to the side surface of the projection 12 may be formed in the projection 12 which has a pyramid or a cone shape. In this configuration, the center of the projection 12 at the bottom surface may be set to a position different from the center of the supporting surface 11a. Accordingly, the aperture of the through hole 12a which extends from the center of the supporting surface 11a in the normal direction of the supporting surface 11a is formed at the side surface of the projection 12. In this configuration, when the ratio of the area S of the supporting surface 11a to the length H of the projection 12 is in the range described above, the effect similar to (1) is also achieved. Further, according the configuration, the following effect can also be achieved.

(6) The sharpness of the projection 12 for puncturing the skin can be prevented from being reduced compared with the configuration of a microneedle which includes a through hole opened to the projection distal end 12c.

Figure 14:
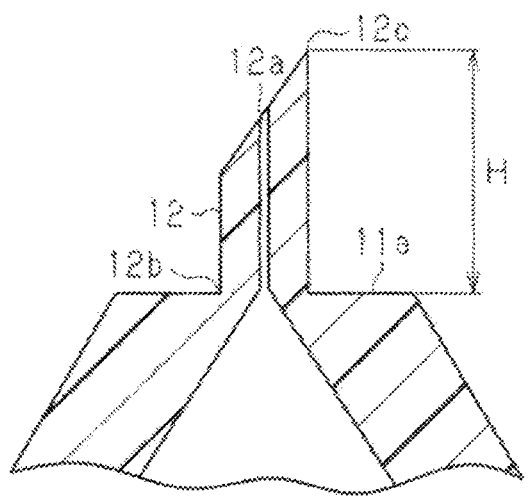
FIG. 14 is a partially enlarged view which illustrates a cross sectional structure of a microneedle according to a modified example.

As shown in FIG. 14, the projection 12 may have a prism or cylinder shape having a tip formed by an inclined surface. The projection distal end 12c is made up of a portion most projected from the supporting surface 11a in the inclined surface, and a portion most projected from the supporting surface 11a in the side surface. The through hole 12a extends from the projection proximal end 12b to the inclined surface, and the aperture of the through hole 12a is formed in the inclined surface. In this configuration, as well, when the ratio of the area S of the supporting surface 11a to the length H of the projection 12 is in the range described above, the effect similar to (1) is also achieved. Further, according to the configuration the following effect can also be achieved.

(7) The diameter of the through hole 12a can be increased while the sharpness of the projection 12 for puncturing the skin can be prevented from being reduced compared with the configuration of a microneedle which includes the through hole 12a opened to the projection distal end 12c.

The microneedle 10 may include two or more projections on the tubular member 11.

Figure 15:
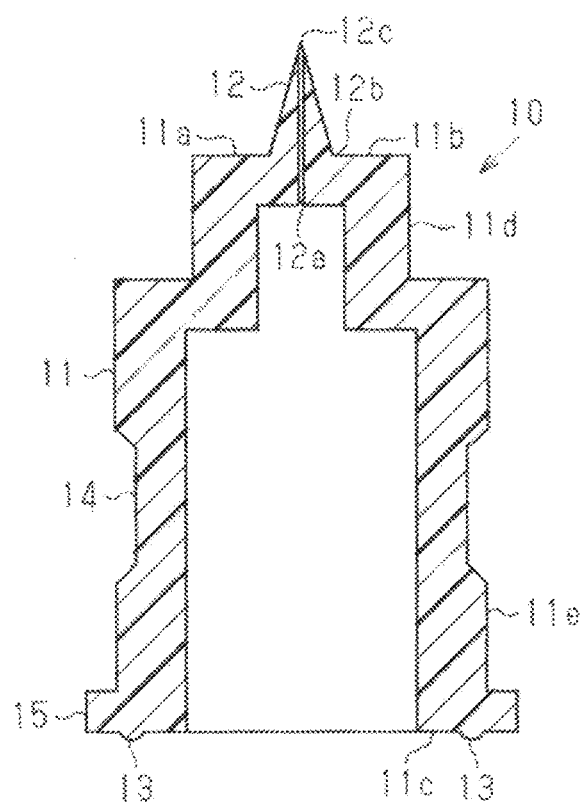
FIG. 15 is a cross sectional view which illustrates a cross sectional structure of a microneedle according to a modified example.

As shown in FIG. 15, the tubular member 11 may have a cylindrical shape with a multiple-stepped portion. The tubular member 11 is in a cylindrical shape with two steps, and the diameter of the tubular member 11 is decreased from the tube proximal end 11c to the tube distal end 11b. In the tubular member 11, the proximal tubular member 11e and the distal tubular member 11d have a hollow cylindrical shape, and the diameter of the distal tubular member 11d is smaller than that of the proximal tubular member 11e. Although the proximal tubular member 11e and the distal tubular member 11d have a hollow cylindrical shape, they may have a hollow prism shape. Alternatively, while the proximal tubular member 11e may have a hollow cylindrical shape, the distal tubular member 11d may have a hollow prism shape. Further, while the proximal tubular member 11e may have a hollow prism shape, the distal tubular member 11d may have a hollow cylindrical shape.

When the resin is injected into the injection mold 30, the tip portion 35b of the core pin 35 may be in contact with the insert 32. As described above, the core pin 35 is preferably not in contact with the insert 32 for the purpose of maintaining the shape of the tip portion 35b of the core pin 35.

An object which is pierced by the microneedle 10 is not limited to a human described above, and may also be other animals.

The configuration of the above embodiment, and each of the configurations of the modified embodiments can be appropriately combined for use.

An aspect of the present invention is to provide a microneedle easily pierced into the skin. One thing to note is that the skin as the puncture target has a certain elasticity, and thus the skin is stretched or contracted due to the force applied to the skin surface by the projection when it is pierced into the skin. Because of this deformation of the skin, which distributes the force applied to the skin surface by the projection, the projection may not be pierced into the skin.

An aspect of a microneedle that addresses the above point is a microneedle including a projection for puncturing the skin, the projection having a through hole that penetrates the projection along an extending direction of the projection; and a tubular member having a supporting surface as an end surface which is a flat surface for supporting the projection and configured to be pressed against the skin to supply a fluid into the through hole of the projection. The projection has a length H that extends along an extending direction of the projection, and the supporting surface has an area S, and the ratio of the area S to the length H (S/H) ranges between 2.1 and 10.5, inclusive.

According to one aspect of the microneedle, since the ratio of the area of the supporting surface to the length of the projection is 2.1 or more, a part of the skin which is punctured by the projection is stretched by the supporting surface when the projection is pressed against the skin. Accordingly, when the projection is pierced into the skin, deformation of the skin by the supporting surface can be prevented. As a result, the projection is easily pierced into the skin. On the other hand, since the ratio of an area of the supporting surface to the length of the projection is 10.5 or less, the depth of a recess of the skin pressed by the supporting surface is likely to be shorter than the length of the projection. Accordingly, the projection is easily pierced into the skin.

In another aspect of the microneedle, the tubular member includes a distal end having the supporting surface, and a proximal end which is an end opposite to the distal end in the extending direction of the tubular member. The tubular member and the projection are preferably integrally formed of resin, and the tubular member preferably has a gate mark at the portion closer to the proximal end than to the center of the tubular member in the extending direction of the tubular member.

According to another aspect of the microneedle, when forming a microneedle made of resin, a gate for injecting resin into a mold is formed at a portion of the mold which is closer to the proximal end than to the center of the tubular member in the extending direction of the tubular member. Consequently, since a distance from the gate to the projection which has the finest structure in the microneedle becomes so large that more of the resin is injected into the portion of the mold which corresponds to the projection, the shape of the microneedle, especially the shape of the projection, conforms to the mold with high precision.

In another aspect of the microneedle, the tubular member preferably includes a flange that extends outward from the outer peripheral surface of the proximal end.

In another aspect of the microneedle, the tubular member preferably includes a distal end having the supporting surface, a proximal end which is opposite to the distal end in the extending direction of the tubular member and a flange that extends outward from the outer peripheral surface of the proximal end.

For example, the microneedle is used for intracutaneous administration of drug solution with being attached to a syringe barrel instead of injection needles. In this regard, according to another aspect of the microneedle, the microneedle can be attached to and removed from a Luer-lock type syringe barrel.

In another embodiment of the microneedle, the outer peripheral surface of the tubular member preferably has a recess.

According to another embodiment of the microneedle, since a tool or a human finger for holding the microneedle can fit into the recess, the microneedle can be easily held by the tool or the human finger compared with the configuration of a microneedle which does not include the recess.

In another embodiment of the microneedle, the tubular member preferably has a tapered shape toward the supporting surface.

According to another embodiment of the microneedle, the tubular member 11 gradually becomes thicker toward the end further from the supporting surface which requires a fine processing, thereby enhancing the formability of the structure of the tubular member except for the projection and the supporting surface.

In another embodiment of the microneedle, the projection may be a pyramid or a cone shape having a projection proximal end connected to the supporting surface, and the through hole may extend from the projection proximal end to a side surface of the projection.

According to another embodiment of the microneedle, the sharpness of the projection for puncturing the skin can be prevented from being reduced compared with the configuration of a microneedle which includes a through hole opened to a distal end of a projection.

In another embodiment of the microneedle, the projection may have a prism or a cylinder shape having a projection proximal end connected to the supporting surface and a tip formed by an inclined surface, and the through hole may extend from the projection proximal end to the inclined surface.

According to another embodiment of the microneedle, the diameter of the through hole can be increased while the sharpness of the projection for puncturing the skin can be prevented from being reduced compared with the configuration of a microneedle which includes a through hole opened to the distal end of the projection.

The embodiments of the present invention can facilitate piercing a microneedle into the skin.

REFERENCE SIGNS LIST

10 . . . Microneedle, 11 . . . Tubular member, 11a . . . Supporting surface, 11b . . . Tube distal end, 11c . . . Tube proximal end, 11d . . . Distal tubular member, 11e . . . Proximal tubular member, 12 . . . Projection, 12a . . . Through hole, 12b . . . Projection proximal end 12c Projection distal end, 13 . . . Gate mark, 14 . . . Recess, 15 . . . Flange, 20 . . . Syringe barrel, 21 . . . External cylinder, 21a . . . Cylinder tip, 22 . . . Plunger, 30 . . . Injection mold, 31 . . . Fixed mold, 32 . . . Insert, 32a . . . Projection forming groove, 33 . . . First movable mold, 33a, 34a . . . Cylinder forming groove, 34 . . . Second movable mold, 35 . . . Core pin, 35a . . . Main body, 35b . . . Tip portion, 36 . . . Runner, 37 . . . Gate Obviously, numerous modifications and variations of the present invention are possible in light of the above teachings. It is therefore to be understood that within the scope of the appended claims, the invention may be practiced otherwise than as specifically described herein.

What is claimed is:

1. A microneedle, comprising:
a projection having a through hole such that the through hole is formed to extend in a first direction that the projection extends; and
a tubular member configured to supply a fluid to the through hole of the projection and having an end surface such that the projection is formed on the end surface of the tubular member and that the end surface has a support surface configured to be pressed against a skin when the projection injects the fluid through the through hole to the skin,
wherein the projection is continuously tapered and has a length H has a length H extending from the support surface of the tubular member at one end to a tip end of the projection at an opposite end of the projection along the first direction perpendicular to the support surface of the tubular member, and the supporting surface at the end surface of the tubular member has an area S such that a ratio of S/H is in a range from 2.1 to 10.5.

2. The microneedle of claim 1, wherein the tubular member has the end surface at a distal end and a proximal end opposite to the distal end in a second direction that the tubular member extends, the tubular member and the projection comprise a resin and are integrally formed, and the tubular member has a gate mark at a position closer to the proximal end than to a center of the tubular member in the second direction.

3. The microneedle of claim 2, wherein the tubular member includes a flange that extends outward from an outer peripheral surface of the proximal end.

4. The microneedle of claim 1, wherein the tubular member has the end surface at a distal end and has a proximal end opposite to the distal end in a second direction that the tubular member extends, and the tubular member further includes a flange that extends outward from an outer peripheral surface of the proximal end.

5. The microneedle of claim 1, wherein the tubular member has a recess on an outer peripheral surface thereof.

6. The microneedle of claim 2, wherein the tubular member has a recess on an outer peripheral surface thereof.

7. The microneedle of claim 3, wherein the tubular member has a recess on an outer peripheral surface thereof.

8. The microneedle of claim 4, wherein the tubular member has a recess on an outer peripheral surface thereof.

9. The microneedle of claim 1, wherein the tubular member has a shape tapered toward the end surface.

10. The microneedle of claim 2, wherein the tubular member has a shape tapered toward the end surface.

11. The microneedle of claim 3, wherein the tubular member has a shape tapered toward the end surface.

12. The microneedle of claim 4, wherein the tubular member has a shape tapered toward the end surface.

13. The microneedle of claim 5, wherein the tubular member has a shape tapered toward the end surface.

14. The microneedle of claim 1, wherein the projection has a pyramid or cone shape with a projection proximal end connected to the end surface of the tubular member, and the projection has the through hole extended from the projection proximal end to a side surface of the projection.

15. The microneedle of claim 2, wherein the projection has a pyramid or cone shape with a projection proximal end connected to the end surface of the tubular member, and the projection has the through hole extended from the projection proximal end to a side surface of the projection.

16. The microneedle of claim 3, wherein the projection has a pyramid or cone shape with a projection proximal end connected to the end surface of the tubular member, and the projection has the through hole extended from the projection proximal end to a side surface of the projection.

17. The microneedle of claim 4, wherein the projection has a pyramid or cone shape with a projection proximal end connected to the end surface of the tubular member, and the projection has the through hole extended from the projection proximal end to a side surface of the projection.

18. The microneedle of claim 1, wherein the projection has a prism or cylinder shape with a projection proximal end connected to the end surface of the tubular member, the projection has a tip portion having an inclined surface, and the projection has the through hole extended from the projection proximal end to the inclined surface.

19. The microneedle of claim 2, wherein the projection has a prism or cylinder shape with a projection proximal end connected to the end surface of the tubular member, the projection has a tip portion having an inclined surface, and the projection has the through hole extended from the projection proximal end to the inclined surface.

20. The microneedle of claim 3, wherein the projection has a prism or cylinder shape with a projection proximal end connected to the end surface of the tubular member, the projection has a tip portion having an inclined surface, and the projection has the through hole extended from the projection proximal end to the inclined surface.

* * * * *